United States Patent
Christadoss

(10) Patent No.: US 10,093,743 B2
(45) Date of Patent: Oct. 9, 2018

(54) MUSCLE SPECIFIC TYROSINE KINASE-FLUOROPHORE CONJUGATE COMPOSITIONS, KITS AND METHODS OF USING

(71) Applicant: Premkumar Christadoss, League City, TX (US)

(72) Inventor: Premkumar Christadoss, League City, TX (US)

( * ) Notice: Subject to any disclaimer, the term of this patent is extended or adjusted under 35 U.S.C. 154(b) by 0 days.

(21) Appl. No.: 14/835,934

(22) Filed: Aug. 26, 2015

(65) Prior Publication Data

US 2016/0137741 A1 May 19, 2016

Related U.S. Application Data

(60) Provisional application No. 62/081,170, filed on Nov. 18, 2014.

(51) Int. Cl.
| | | |
|---|---|---|
| *A61K 49/00* | (2006.01) | |
| *C07K 16/28* | (2006.01) | |
| *C12N 9/12* | (2006.01) | |
| *G01N 33/569* | (2006.01) | |
| *G01N 33/68* | (2006.01) | |

(52) U.S. Cl.
CPC ............ *C07K 16/2887* (2013.01); *C12N 9/12* (2013.01); *G01N 33/56972* (2013.01); *G01N 33/6887* (2013.01); *C12Y 207/10* (2013.01); *G01N 2333/91215* (2013.01)

(58) Field of Classification Search
CPC ............... C12N 9/12; G01N 33/56972; G01N 33/6887; G01N 33/564; G01N 2333/91215; A61K 51/00; A61K 51/08; A61K 51/088; A61K 38/00; A61K 2123/00; A61K 2121/00; A61K 51/0497; A61K 38/43; C07K 16/2887; C12Y 207/10
USPC ........ 424/1.11, 1.65, 1.69, 9.1, 9.2, 9.3, 9.4, 424/9.5, 9.6; 436/506
See application file for complete search history.

(56) References Cited

U.S. PATENT DOCUMENTS

| | | | | |
|---|---|---|---|---|
| 7,267,820 B2* | 9/2007 | Vincent | .................. | C07K 16/28 424/130.1 |
| 7,923,010 B2* | 4/2011 | Christadoss | ........... | C07K 16/18 424/133.1 |
| 8,501,705 B2* | 8/2013 | Christadoss | ......... | A61K 31/713 435/455 |
| 8,530,245 B2* | 9/2013 | Christadoss | ......... | G01N 33/564 436/501 |
| 2010/0203529 A1* | 8/2010 | Kuslich | ................ | C12Q 1/6886 435/6.12 |
| 2013/0108616 A1* | 5/2013 | Mei | ...................... | C12Q 1/6883 424/130.1 |

OTHER PUBLICATIONS

Link et al (J. Clin. Invest., 1991, vol. 87, pp. 2191-2196).*
Im et al (FASEB J., 2001, vol. 15, pp. 2140-2148).*
Dalakas (Nature Clinical Practice Neurology, 2008, vol. 4, No. 10, pp. 557-567).*
Dalakas, Nature Clinical Practice Neurology, 2008, vol. 4, No. 10, pp. 557-567.*
Matthews et al, Clinica Chimica Acta, 2004, vol. 348, pp. 95-99.*

* cited by examiner

*Primary Examiner* — D. L. Jones
(74) *Attorney, Agent, or Firm* — Benjamin Aaron Adler

(57) ABSTRACT

Provided herein is a method of diagnosing muscle specific tyrosine kinase specific autoimmune myasthenia gravis in an individual. Generally, in the method a level of muscle specific tyrosine kinase binding to B cells is determined in a sample from an individual. A significant increase in the level of muscle specific tyrosine kinase reactive B-cells compared to that in a healthy individual indicates the presence of muscle specific tyrosine kinase autoimmune myasthenia gravis. Also provided is a fluorophore-muscle specific tyrosine kinase conjugate and a kit comprising the same useful to test the frequency of muscle specific tyrosine kinase binding B cells expressing specific markers, for diagnosis or as biomarker for muscle specific tyrosine kinase autoimmune myasthenia gravis.

10 Claims, 8 Drawing Sheets

Specification includes a Sequence Listing.

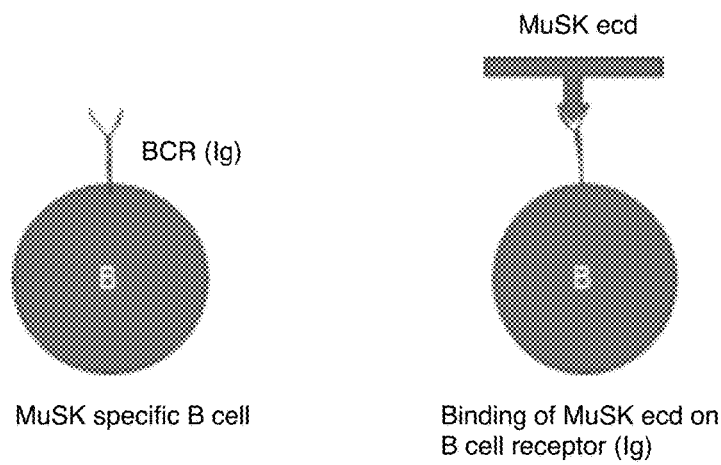

MuSK specific B cell     Binding of MuSK ecd on B cell receptor (Ig)

FIG. 1

MuSK-ecd
→

EFLPKAPVITTPLETVDALVEEVATFMCAVESYPQPEISWTRNKILIKLFDTRYSIREN
GQLLTILSVEDSDDGIYCCTANNGVGGAVESCGALQVKMKPKITRPPINVKIIEGLK
AVLPCTTMGNPKPSVSWIKGDSPLRENSRIAVLESGSLRIHNVQKEDAGQYRCVA
KNSLGTAYSKVVKLEVEVFARILRAPESHNVTFGSFVTLHCTATGIPVPTITWIENGN
AVSSGSIQESVKDRVIDSRLQLFITKPGLYTCIATNKHGEKFSTAKAAATISIAEWSK
PQKDNKGYCAQYRGEVCNAVLAKDALVFLNTSYADPEEAQELLVHTAWNELKVVS
PVCRPAAEALLCNHIFQECSPGVVPTPIPICREYCLAVKELFCAKEWLVMEEKTHR
GLYRSEMHLLSVPECSKLPSMHWDPTACARLPHLAFPPMTSSKPSVDIPNLPSSS
SSSFSVSPAAASFLEQKLISEEDLNSAVDHHHHHH     (SEQ ID NO: 1)
←

MuSK-ecd     myc-epitope     His-tag

FIG. 2

MUSCLE SPECIFIC TYROSINE KINASE-FLUOROPHORE CONJUGATE COMPOSITIONS, KITS AND METHODS OF USING

CROSS-REFERENCE TO RELATED APPLICATION

This non-provisional application claims benefit of provisional application U.S. Ser. No. 62/081,170 filed Nov. 18, 2014, now abandoned, the entirety of which is hereby incorporated by reference.

BACKGROUND OF THE INVENTION

Field of the Invention

The present invention relates generally to the field of diagnostic methods and biomarkers relating to myasthenia gravis. More specifically, the present invention relates to muscle specific tyrosine kinase-fluorophore conjugates compositions, kits and methods of using the compositions.

Description of the Related Art

Myasthenia gravis is a neuromuscular disorder characterized by weakness and fatigability of skeletal muscles. The underlying defect is a decrease in the number of available acetylcholine receptors at neuromuscular junctions due to an antibody-mediated autoimmune attack. In the neuromuscular junction, acetylcholine is synthesized in the motor nerve terminal and stored in vesicles (quanta). When an action potential travels down a motor nerve and reaches the nerve terminal, acetylcholine from 150 to 200 vesicles is released and combines with acetylcholine receptors that are densely packed at the peaks of postsynaptic folds. When acetylcholine combines with the binding sites on the acetylcholine receptor, the channels in the acetylcholine receptors open, permitting the rapid entry of cations, chiefly sodium, which produces depolarization at the end-plate region of the muscle fiber. If the depolarization is sufficiently large, it initiates an action potential that is propagated along the muscle fiber, triggering muscle contraction. This process is rapidly terminated by hydrolysis of acetylcholine by acetylcholinesterase and by diffusion of acetylcholine away from the receptor.

In myasthenia gravis, the fundamental defect is a decrease in the number of available acetylcholine receptors at the postsynaptic muscle membrane. In addition, the postsynaptic folds are flattened, or "simplified." These changes result in decreased efficiency of neuromuscular transmission. Therefore, although acetylcholine is released normally, it produces small end-plate potentials that may fail to trigger muscle action potentials. Failure of transmission at many neuromuscular junctions results in weakness of muscle contraction.

The neuromuscular abnormalities in myasthenia gravis are brought about by an autoimmune response mediated by specific anti-acetylcholine receptor antibodies. The anti-acetylcholine receptor antibodies are called pathogenic antibodies and reduce the number of available acetylcholine receptors at neuromuscular junctions by three distinct mechanisms: (1) accelerated turnover of acetylcholine receptors by a mechanism involving cross-linking and rapid endocytosis of the receptors; (2) blockade of the active site of the acetylcholine receptor, i.e., the site that normally binds acetylcholine; and (3) damage to the postsynaptic muscle membrane by the antibody in collaboration with complement. The pathogenic antibodies are IgG and are T-cell dependent.

The clinical manifestations of the autoimmune disease myasthenia gravis are correlated with the presence of these pathogenic antibodies located at the neuromuscular junction. Up to date, only a few therapies exist, which are either symptomatic treatment or immunotherapy.

Seventy percent of patients with myasthenia gravis carry autoantibodies to the acetylcholine receptor and a separate 5-10% carry autoantibodies to muscle specific tyrosine kinase (Vincent and Leite, 2005, Curr Opin Neurol; 18(5): 519-25). Symptoms of patients with muscle specific tyrosine kinase related myasthenia gravis include fatigue, muscle weakness, double vision, drooping eyelids, and difficulty chewing or swallowing and in severe disease paralysis and respiratory distress. Muscle specific tyrosine kinase antibodies are mainly of the non-complement-fixing IgG4 isotype. Muscle specific tyrosine kinase-myasthenia gravis is most commonly diagnosed by RIA/ELISA. Electrophysiological studies, such as single-fiber electromyography, are often used to diagnose acetylcholine receptor-seronegative myasthenia gravis. However, these studies are time-consuming, require specialized expertise, have limited availability, and are unpleasant for patients. The limitations of this assay are a prolonged turnaround time and few labs offering the test. Serum muscle specific tyrosine kinase antibody concentrations are also not a reliable marker for disease activity or severity.

There is a recognized need, therefore, for muscle specific tyrosine kinase-fluorophore conjugates compositions and kits and methods of using the compositions in the diagnosis of myasthenia gravis. The present invention fulfills this longstanding need and desire in the art.

SUMMARY OF THE INVENTION

The present invention is directed to a conjugate comprising muscle specific tyrosine kinase coupled to a detectable moiety.

The present invention also is directed to a method of diagnosing muscle specific tyrosine kinase autoimmune myasthenia gravis in an individual. The method comprises the steps of obtaining a sample comprising B cells from the individual and from a healthy control individual. The sample from the individual sample and the healthy control sample are contacted with a human muscle specific tyrosine kinase conjugate described herein and a level of muscle specific tyrosine kinase binding to B cells in the samples is measured. A significant increase in the level of muscle specific tyrosine kinase reactive B-cells compared to a level of muscle specific tyrosine kinase reactive B-cells in the healthy control sample indicates the presence of muscle tyrosine kinase specific autoimmune myasthenia gravis.

The present invention is directed to a method for diagnosing muscle specific tyrosine kinase autoimmune myasthenia gravis in an individual. The method comprises the steps of obtaining a sample comprising B cells from the individual and from a healthy control individual. The individual sample and the healthy control sample are contacted with a B cell marker binding agent a level of binding of the B cell marker binding agent to the B cells from the samples is measured. An increase in the binding level in the individual sample compared to the binding level in the healthy control indicates increased muscle specific tyrosine kinase specific B cells that produces pathogenic muscle specific tyrosine kinase antibodies for muscle specific tyrosine kinase myasthenia gravis.

The present invention is further directed to a method for monitoring muscle specific tyrosine kinase binding specific B cells in vivo in muscle specific tyrosine kinase myasthenia gravis patient. The method comprises injecting intravenously a fluorescent conjugated muscle specific tyrosine kinase into a subject and imaging the whole body of the subject with a fluorescence enabled imaging system. An intensity of the fluorescence emitted during the whole body imaging is measured where the intensity indicates the level of muscle specific tyrosine kinase binding specific B cells in vivo in muscle specific tyrosine kinase myasthenia gravis.

The present invention is also directed to a kit for detecting muscle specific tyrosine kinase reactive B cells comprising a conjugate comprising muscle specific tyrosine kinase and a detectable moiety.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1 illustrates specific binding of muscle specific tyrosine kinase Extracellular Domain (MuSK ECD) on the B cell receptor (surface immunoglobulin Ig) of muscle specific tyrosine kinase myasthenia gravis patient's B cell.

FIG. 2 is the Human muscle specific tyrosine kinase Extracellular Domain amino acid sequence (SEQ ID NO: 1).

FIG. 3A shows IgG+ isotype of B cells in muscle specific tyrosine kinase-immunized mice. FIG. 3B shows IgG1+ isotype of B cells in muscle specific tyrosine kinase-immunized mice. FIG. 3C shows IgG2b+ isotype of B cells in muscle specific tyrosine kinase-immunized mice. FIG. 3D shows IgG3+ isotype of B cells in muscle specific tyrosine kinase-immunized mice. FIG. 3E shows muscle specific tyrosine kinase-binding to IgG+ B cells of muscle specific tyrosine kinase-immunized mice. FIG. 3F shows muscle specific tyrosine kinase-binding to IgG1+ B cells of muscle specific tyrosine kinase-immunized mice. FIG. 3G shows muscle specific tyrosine kinase-binding to IgG2b+ B cells of muscle specific tyrosine kinase-immunized mice. FIG. 3H shows muscle specific tyrosine kinase-binding to IgG3+ B cells of muscle specific tyrosine kinase-immunized mice. FIG. 3I shows muscle specific tyrosine kinase-binding to CD45R+ B cells of muscle specific tyrosine kinase-immunized mice.

FIG. 4A shows IgG+ isotype of B cells in CFA-immunized mice. FIG. 4B shows IgG1+ isotype of B cells in CFA-immunized mice. FIG. 4C shows IgG2b+ isotype of B cells in CFA-immunized mice. FIG. 4D shows IgG3+ isotype of B cells in CFA-immunized mice. FIG. 4E shows muscle specific tyrosine kinase-binding to IgG+ B cells of CFA-immunized mice. FIG. 4F shows muscle specific tyrosine kinase-binding to IgG1+ B cells of CFA-immunized mice. FIG. 4G shows muscle specific tyrosine kinase-binding to IgG2b+ B cells of CFA-immunized mice. FIG. 4H shows muscle specific tyrosine kinase-binding to IgG3+ B cells of CFA-immunized mice. FIG. 4I shows muscle specific tyrosine kinase-binding to CD45R+ B cells of CFA-immunized mice.

FIG. 5A shows OVA-binding to IgG+ B cells of muscle specific tyrosine kinase-immunized mice. FIG. 5B shows OVA-binding to IgG1+ B cells of muscle specific tyrosine kinase-immunized mice. FIG. 5C shows OVA-binding to IgG2b+ B cells of muscle specific tyrosine kinase-immunized mice. FIG. 5D shows OVA-binding to IgG3+ B cells of muscle specific tyrosine kinase-immunized mice. FIG. 5E shows OVA-binding to CD45R+ B cells of muscle specific tyrosine kinase-immunized mice.

FIG. 6A shows OVA-binding to IgG+ B cells of CFA-immunized mice. FIG. 6B shows OVA-binding to IgG1+ B cells of CFA-immunized mice. FIG. 6C shows OVA-binding to IgG2b+ B cells of CFA-immunized mice. FIG. 6D shows OVA-binding to IgG3+ B cells of CFA-immunized mice. FIG. 6E shows OVA-binding to CD45R+ B cells of CFA-immunized mice.

FIG. 7A is the result of side scatter for the unstained blood samples. FIG. 7B is the result of side scatter for the muscle specific tyrosine kinase Alexa-647 stained blood sample. FIG. 7C is a histogram figure for the numbers of cells in two groups with the different fluorescent levels, showing muscle specific tyrosine kinase-specific B cells with a high fluorescent intensity.

DETAILED DESCRIPTION OF THE INVENTION

Figure 3A:
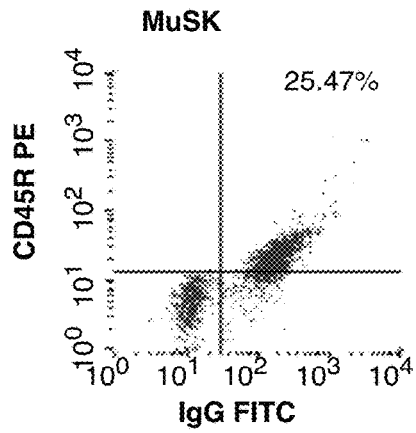
FIGS. 3A-3I illustrate that muscle specific tyrosine kinase-immunized mice show distinct and prominent CD45R+, IgG+, IgG1+, IgG2b+ and IgG3+ B cell populations binding with Alexa-muscle specific tyrosine kinase (MuSK-ALEXA 647).
Figure 3B:
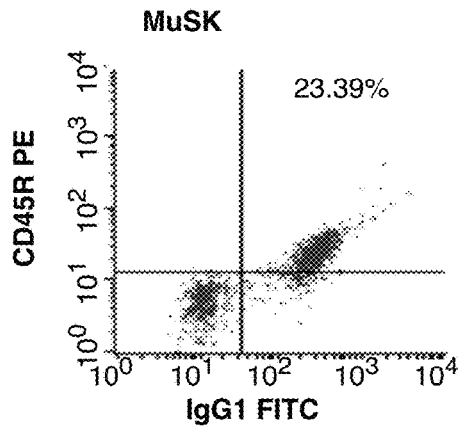
Figure 3C:
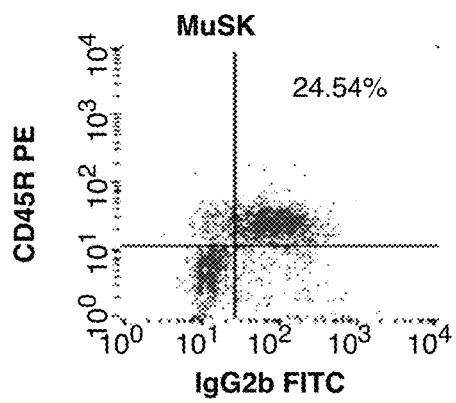
Figure 3D:
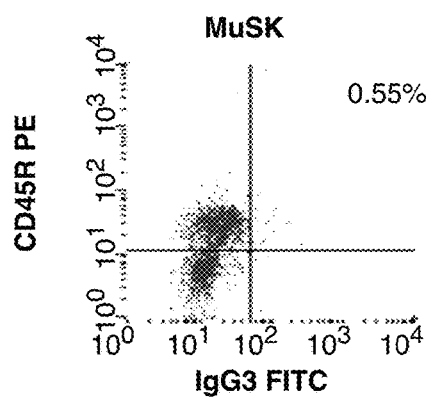
Figure 3E:
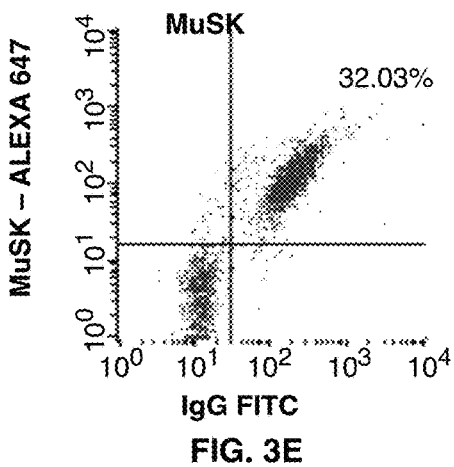
Figure 3F:
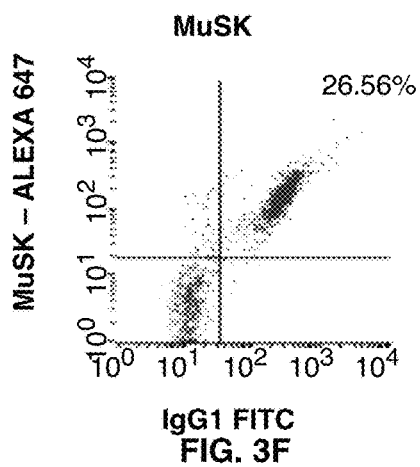
Figure 3G:
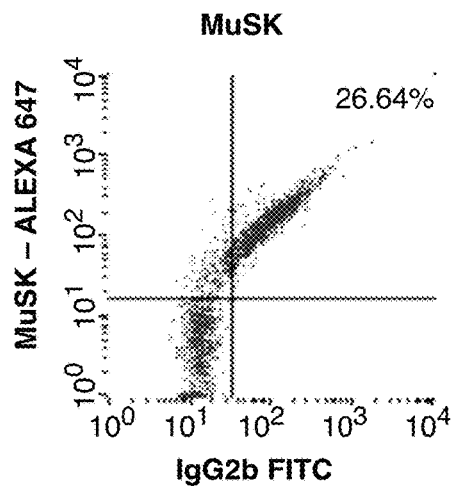
Figure 3H:
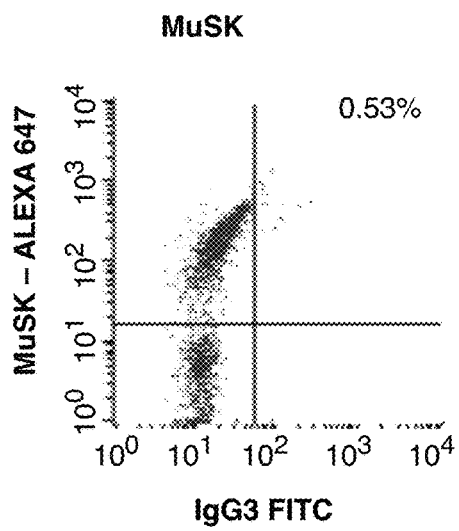
Figure 3I:
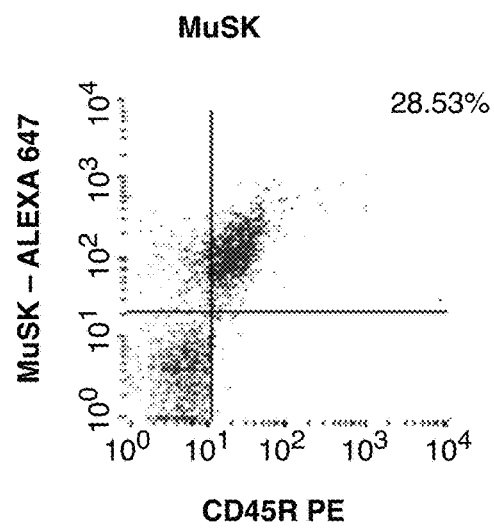
Figure 4A:
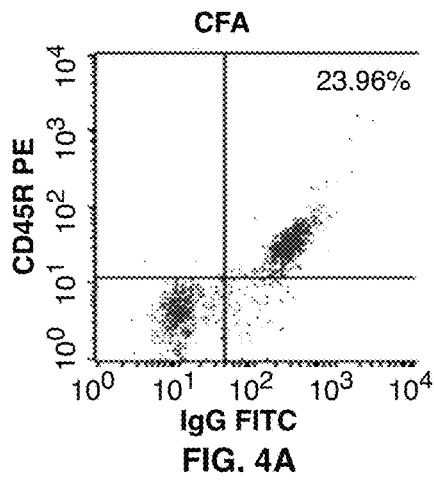
FIGS. 4A-4I illustrate that CFA-immunized mice peripheral blood mononuclear cells subgroups do not show any appreciable binding with Alexa-muscle specific tyrosine kinase (MuSK-ALEXA 647).
Figure 4B:
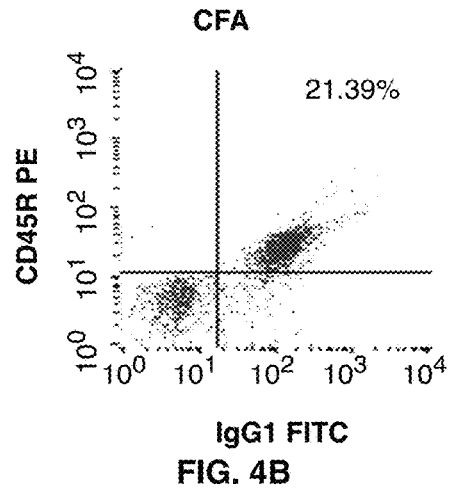
Figure 4C:
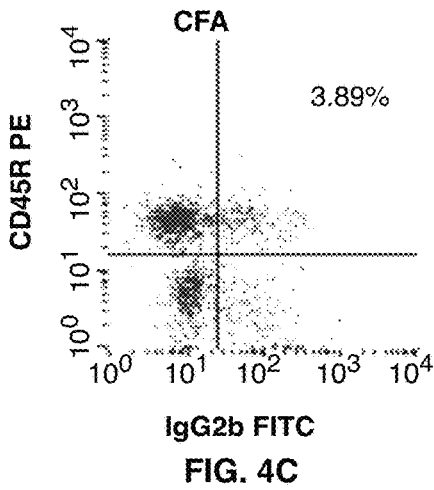
Figure 4D:
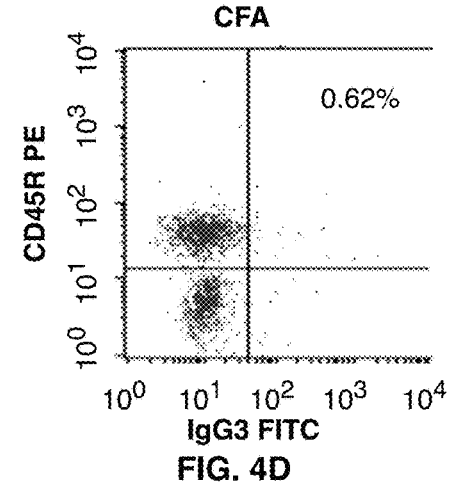
Figure 4E:
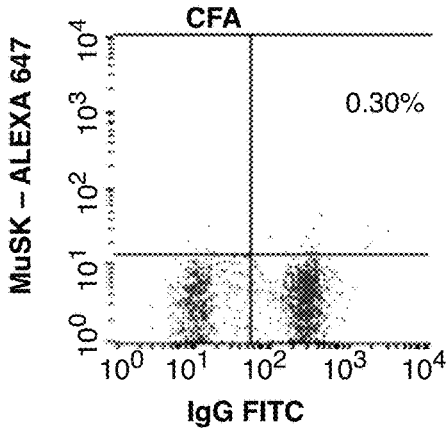
Figure 4F:
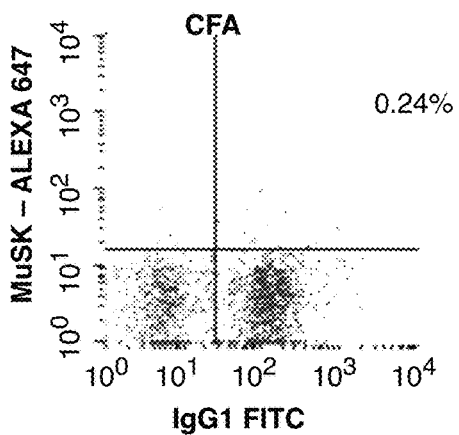
Figure 4G:
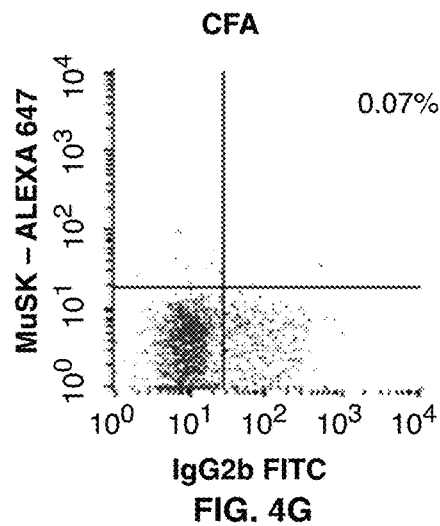
Figure 4H:
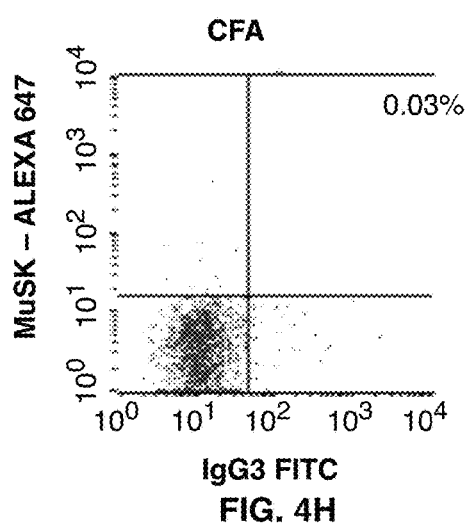
Figure 4I:
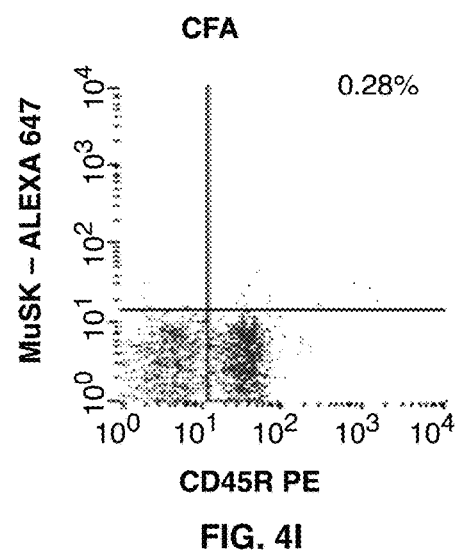
Figure 5A:
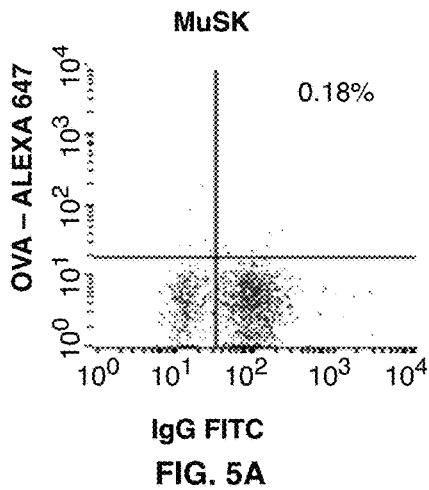
FIGS. 5A-5E illustrate that muscle specific tyrosine kinase-immunized mice peripheral blood mononuclear cells subgroups do not show any remarkable binding with Alexa-OVA (OVA-ALEXA 647).
Figure 5B:
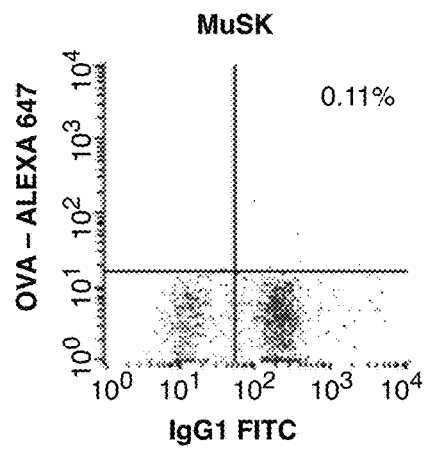
Figure 5C:
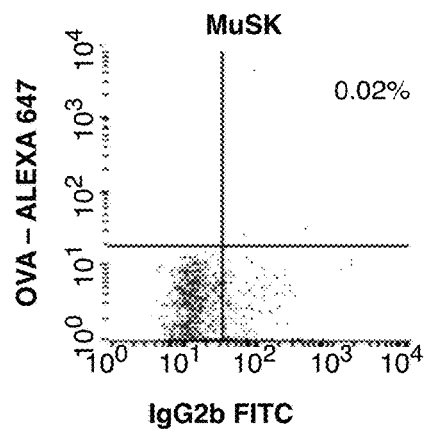
Figure 5D:
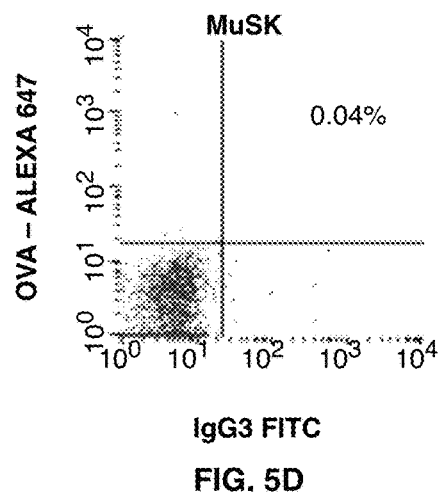
Figure 5E:
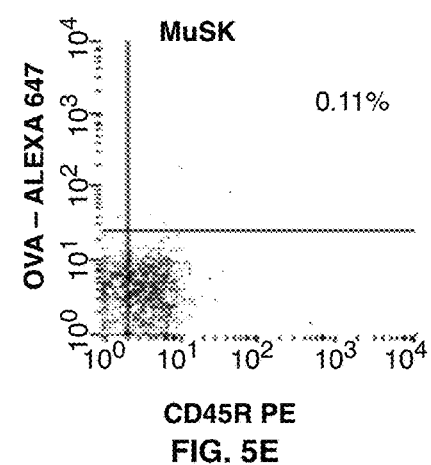
Figure 6A:
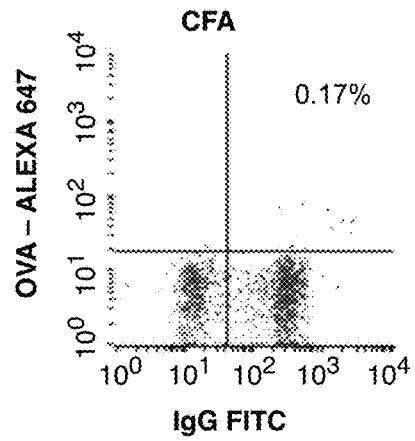
FIGS. 6A-6E illustrate that CFA-immunized mice peripheral blood mononuclear cells subgroups do not show any remarkable binding with Alexa-OVA (OVA-ALEXA 647).
Figure 6B:
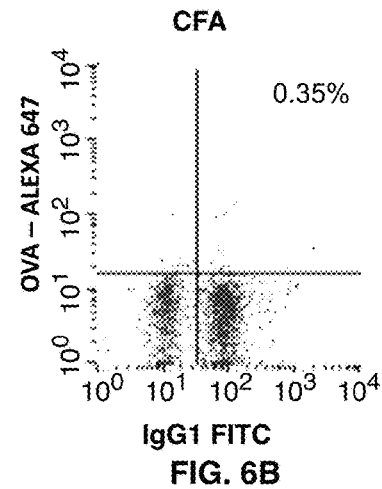
Figure 6C:
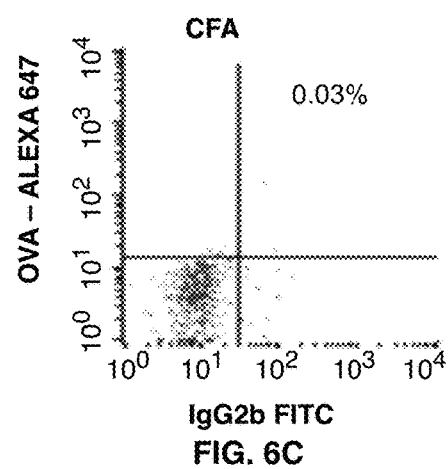
Figure 6D:
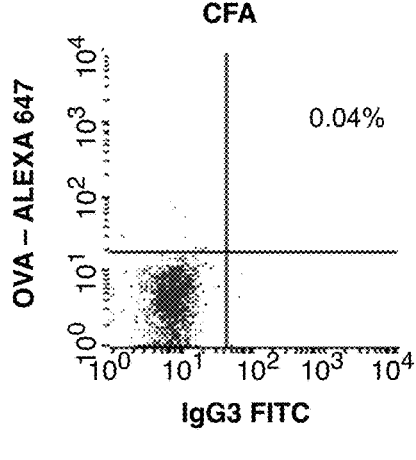
Figure 6E:
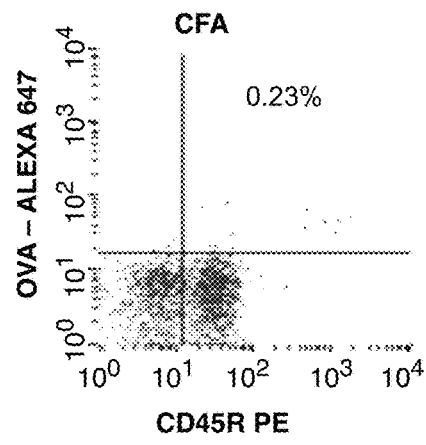

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The characterization of B cells specific for the production of pathogenic antibodies to muscle specific tyrosine kinase is one of the most important areas in myasthenia gravis research. The present invention demonstrates a diagnostic biomarker for muscle specific tyrosine kinase-myasthenia gravis by using Alexa fluorophore-conjugated muscle specific tyrosine kinase as a probe for identifying potentially pathogenic peripheral blood, muscle tyrosine kinase-specific B cells in human myasthenia gravis by flow cytometry.

The present invention provides a biomarker flow cytometry assay for muscle specific tyrosine kinase myasthenia gravis, which identifies muscle specific tyrosine kinase-binding, IgG4-expressing B cells or to IgM or other IgG isotypes expressing B cells. The biomarker flow cytometry assay for muscle specific tyrosine kinase-myasthenia gravis of the present invention allows a person of ordinary skill in this art to examine the frequency of muscle specific tyrosine kinase-specific B cells in the muscle specific tyrosine kinase-myasthenia gravis patients and seronegative MG patients. This biomarker flow cytometry assay has several distinct advantages over current diagnostic tests for muscle specific tyrosine kinase-myasthenia gravis, including faster results, use of a technology platform that is widely available, higher sensitivity, and the ability for use as a predictive biomarker (Table 1).

reactive B cells in a blood sample from a patient with suspected or confirmed myasthenia gravis relative to a healthy control. The present invention includes a kit to detect auto-reactive muscle specific tyrosine kinase-specific B cells in patients with myasthenia gravis with a fluorophore-conjugated muscle specific tyrosine kinase. This technique to quantify muscle specific tyrosine kinase-specific B cells relates directly to disease pathogenesis, as these cells produce, besides antibodies, destructive complement and pro-inflammatory cytokines.

Thus, in one embodiment of the present invention, there is provided a method of pharmacodynamic measurement during early phase clinical development. Refractory muscle tyrosine kinase specific-myasthenia gravis has recently been treated by depleting CD20-expressing B cells with the monoclonal antibody rituximab. The fluorophore-muscle specific tyrosine kinase conjugate could be used to test the frequency of pathogenic B cell populations and the extent of muscle specific tyrosine kinase B cell depletion during rituximab treatment. PBMC (Example 3) taken from muscle specific tyrosine kinase myasthenia gravis patient before and after rituximab treatment could be tested for the presence and/or number of muscle specific tyrosine kinase-reactive B

TABLE 1

|  | Anti-MuSK antibody assay | MuSK-binding B cell flow cytometry |
| --- | --- | --- |
| Radioactivity | Yes | No |
| Availability | Very few labs | Common Technology |
| Assay turnaround time | 7-14 days | 1 day |
| Prognostic biomarker | No | Yes |
| Predictive of therapeutic response | No | Yes |
| Therapy with rituximab (B cell depletion) | Not a marker | Marker for AChR specific B cells |
| Predictive biomarker of relapse | No | Yes |
| Early diagnosis | Not possible, no antibodies are in circulation; sometimes months to a year after MG symptoms | Possible, self reactive B cells are in circulation before and at the time of MG symptoms |
| Marker of disease severity, clinical status | No, serum AChR antibody concentrations are not a reliable marker for disease activity or severity | Yes, predict correlation of AChR-binding B cell frequency with disease severity |
| Patient outcomes | Poor, delay in diagnosing & initiation of therapy | Improved: faster, early diagnosis and initiation of therapy |
| Seronegative MG 10% of MG patients do not have auto-antibodies detectable with ~50% of patients with ocular MG | Negative | Could be positive since self reactive B cells are in the circulation when symptoms are observed - thus aids in the diagnosis |

FIG. 1 illustrates how B cells specific for muscle specific tyrosine kinase can bind muscle specific tyrosine kinase Extracellular Domain (MuSK ECD) on its B cell receptor, which is the surface immunoglobulin on the B cell. For example, the muscle specific tyrosine kinase specific B cells may bind a muscle specific tyrosine kinase Extracellular Domain with a sequence shown in SEQ ID NO: 1 (FIG. 2). The increased frequency of muscle specific tyrosine kinase specific B cells can be detected by staining of muscle specific tyrosine kinase myasthenia gravis B cells with Alexa-muscle specific tyrosine kinase Extracellular Domain and analyzed via flow cytometry.

Antigen-Specific Approaches to Biomarker Development Improve Myasthenia Gravis Diagnosis and Management The methods of the present invention quantify the presence and/or number of muscle specific tyrosine kinase-reactive B cells. The extent of depletion of muscle specific tyrosine kinase-reactive B cells could be correlated with clinical severity. Thus the muscle specific tyrosine kinase binding B cells will serve as an ideal marker for response the B cell depletion therapy in muscle specific tyrosine kinase myasthenia gravis. This would be an improvement over existing monitoring that simply follows total CD20 B cell levels. The fluorophore-muscle specific tyrosine kinase conjugate will provide information about the type of cells producing anti-muscle specific tyrosine kinase antibodies, such as antibody class, frequency of these specific B cells, and maturation status of B cells. In addition, other cells that can be detected using the fluorophore-muscle specific tyrosine kinase conjugate include anti-muscle specific tyrosine kinase antibody-secreting B cells expressing IgG1, IgG2, IgG3 and IgG4 isotypes; B cells expressing CD21 (activation marker), $CD38^{hi}CD20^{-CD}27^{hi}CD21^{lo}$; naive B cells (CD19+ CD27− $CD21^{hi}CD38^{lo}$); memory B cells (CD19+CD38+CD138+ CD27+), and possibly plasma cells. This technique will also be a useful tool for academic researchers studying muscle specific tyrosine kinase-myasthenia gravis pathogenesis.

In one embodiment of the present invention, there is provided a conjugate comprising muscle specific tyrosine kinase coupled to a detectable moiety. In this embodiment, the detectable moiety is a fluorophore. The fluorophore can be an Alexa fluorophore such as Alexa-488 and Alexa-647.

In this embodiment, the muscle specific tyrosine kinase comprises at least 5 consecutive amino acids of a muscle tyrosine kinase polypeptide. The muscle specific tyrosine kinase may comprise an extracellular domain. The extracellular domain may have a sequence as shown in SEQ ID NO: 1.

In another embodiment of the present invention, there is provided a method of using the Alexa-muscle specific tyrosine kinase conjugate to test the frequency of muscle specific tyrosine kinase specific B cells expression in various cellular molecules during stages of development in various animal models of myasthenia gravis. Further provided is a method of using the Alexa-muscle specific tyrosine kinase conjugate to deplete muscle specific tyrosine kinase specific B cells in vitro. The present invention further provides methods of studying gene expression profiles including transcriptomics in muscle specific tyrosine kinase specific B cells in animal models of myasthenia gravis and human myasthenia gravis.

Thus, the present invention is directed to a method of diagnosing muscle specific tyrosine kinase autoimmune myasthenia gravis in an individual, comprising the steps of obtaining a sample comprising B cells from the individual and from a healthy control individual; contacting the individual sample and the healthy control sample from the individual with a human muscle specific tyrosine kinase-fluorophore conjugate and measuring a level of muscle specific tyrosine kinase binding to B cells in the sample, where a significant increase in the level of muscle specific tyrosine kinase reactive B-cells compared to the level of muscle specific tyrosine kinase reactive B-cells in the healthy control sample from indicates the presence of muscle specific tyrosine kinase autoimmune myasthenia gravis. Representative samples, include but are not limited to, blood, peripheral blood cells, lymph node cells, peripheral blood lymphocytes, thymic cells and purified B cells. Preferably, the muscle specific tyrosine kinase conjugate comprises a fluorophore. A representative example of a useful fluorophore is an Alexa fluorophore such as Alexa-488 or Alexa-647. A representative manner, mode or process for measuring the level of muscle specific tyrosine kinase binding B cells is by flow cytometry. An ELISA or a Lateral Flow Cytometry assay may be alternatives.

The present invention is further directed to a method for testing the response of a patient with myasthenia gravis or experimental autoimmune myasthenia gravis to a therapy. This method comprises the steps of administering a therapy to a patient with myasthenia gravis or experimental autoimmune myasthenia gravis; measuring an amount of muscle specific tyrosine-reactive B cells in peripheral blood mononuclear cell samples from the muscle specific tyrosine kinase myasthenia gravis patient after the therapy, wherein a depletion of muscle specific tyrosine kinase-reactive B cells indicates a positive response of the patient with myasthenia gravis or experimental autoimmune myasthenia gravis to the therapy.

The present invention is directed to another method for diagnosing muscle specific tyrosine kinase autoimmune myasthenia gravis in an individual. The method comprises the steps of obtaining a sample comprising B cells from the individual and from a healthy control individual; contacting the sample from the individual sample and the healthy control sample with a B cell marker binding agent; and measuring the level of the B cell marker binding agent that binds to the B cells from the individual sample and from the healthy control sample. An increase in the binding level in the individual sample compared to the binding level in the healthy control indicates increased muscle specific tyrosine kinase specific B cells that produces pathogenic muscle specific tyrosine kinase antibodies for muscle specific tyrosine kinase myasthenia gravis.

Preferably, the B cell marker binding agent is an antibody and the B cell marker is a cell surface molecule or an intracelullar molecule. Generally, the antibody binds IgG, IgG1, IgG2, IgG3, IgG4, CD19, CD21, CD45R, CD20, CD22, CD23, or CD81.

The present invention is further directed to a kit for detecting muscle specific tyrosine kinase reactive B cells comprising a muscle specific tyrosine kinase conjugate. Preferably, the muscle specific tyrosine kinase conjugate comprises a fluorophore. A representative example of a useful fluorophore is an Alexa fluorophore such as Alexa-488 or Alexa-647.

The present invention is further directed to a method for monitoring muscle specific tyrosine kinase binding specific B cells in vivo in muscle specific tyrosine kinase myasthenia gravis. This method comprises the steps of injecting a fluorescent conjugated muscle specific tyrosine kinase in to a subject intravenously; imaging for whole body of the subject with a fluorescence enabled imaging system; and measuring the intensity of the fluorescence emitted during the whole body imaging. The intensity of fluorescence indicates the level of muscle specific tyrosine kinase binding specific B cells in vivo in muscle specific tyrosine kinase myasthenia gravis.

The present invention is further directed to a kit for detecting muscle specific tyrosine kinase reactive B cells comprising a muscle specific tyrosine kinase conjugate. Preferably, the muscle specific tyrosine kinase conjugate comprises a fluorophore. A representative example of a useful fluorophore is an Alexa fluorophore such as Alexa-488 or Alexa-647.

As described below, the invention provides a number of advantages and several uses, however, such advantages and uses are not limited by such description. Embodiments of the present invention are better illustrated with reference to the Figure(s) and Table(s); however, such reference is not meant to limit the present invention in any fashion. The embodiments and variations described in detail herein are to be interpreted by the appended claims and equivalents thereof.

EXAMPLE 1

Conjugation of Alexa Fluor 647 with Muscle Specific Tyrosine Kinase

The extracellular domain of muscle specific tyrosine kinase was purchased from Dr. Socrates Tzartos, Hellinic Pasteur Institute, Athens, Greece (clone #2, Yeast expressed, Ni-NTA agarose purified). Alexa Fluor-muscle specific tyrosine kinase conjugates were made by mixing muscle specific tyrosine kinase with Alexa Fluor 647 reactive dye (Invitrogen) and incubating the mix for 1 hr at room temperature with constant stirring. The Alexa 647-muscle specific tyrosine kinase conjugates were separated from un-reactive Alexa Fluor by passing the mixture through sieve chromatography column. Small fractions were collected. The recovery of the conjugate in various fractions was monitored on basis of color and the protein contents as determined by Bradford Protein assay (Biorad) using Y-globulin as standard. The fractions with highest protein content and blue color were pooled and adjusted to a protein content of 0.63 mg/ml, aliquoted and stored at −20° C. until further use.

EXAMPLE 2

Sampling

In collaboration with neurologists, blood samples are being collected from muscle specific tyrosine kinase-myasthenia gravis patients and healthy controls. Detailed clinical information, including disease duration, antibody titers, and myasthenia gravis medications are being recorded in a study database, as well as validated clinical outcome measures that include the MGFA Clinical Classification, myasthenia gravis-Activities of Daily Living score, MG-Quality of Life-15, and MG-MMT score.

Immunologic Assays

All flow cytometry assays are performed and Alexa-muscle specific tyrosine kinase and Alexa-OVA conjugate (antigen specificity control) are prepared and provided by Immune Globe Biotech, LLC. Peripheral blood mononuclear cells from each myasthenia gravis patient and control are surface stained with the panel shown in Table 2 and acquired on a BD LSR II flow cytometer.

TABLE 2

B Cell Panel

| Marker | Purpose |
|---|---|
| CD19 | B cell population |
| CD21 | Survival & Activation |
| IgG4 | Ig predominant in muscle specific tyrosine kinase-myasthenia gravis |
| Muscle specific tyrosine kinase | Antigen specificity |
| OVA | Antigen-non specificity |

The results show that detection of muscle specific tyrosine kinase B cells is a novel diagnostic marker in muscle specific tyrosine kinase-myasthenia gravis patients, that is useful at the time of initial clinical evaluation. This assay is also useful in monitoring disease severity and predicting relapses and response to immunosuppressive and Rituximab therapy.

EXAMPLE 3

Frequency of Muscle Specific Tyrosine Kinase Binding B Cell Subsets in Myasthenia Gravis The following procedure is used to demonstrate the frequency of muscle specific tyrosine kinase binding B cell subsets in myasthenia gravis.

1. Collect 3-10 ml of blood in K2EDTA 10 ml BD Vacutainer Tubes (BD-366643, BD Biosciences).
2. Invert tube several times after blood has been collected.
3. Transfer blood to a "Leucosep" tube (VWR) pre-loaded with Ficoll-Paque PLUS (Greiner Bio-One)
4. Centrifuge "Leucosep" tube for 30 min at 800 g with the brake off at 18 to 26° C.
5. Remove plasma from the top layer and aliquot 1 ml×5 into 2 mL cryovial tubes.
6. Transfer PBMC layer to 15 ml conical tube and add HBSS for a final volume of 10 ml.
7. Pellet cells by centrifugation for 10 mins at 350 g at 18 to 26° C.
8. Gently pour the supernatant into waste bottle without disturbing pellet.
9. Resuspend the cells and repeat wash 1×.
10. Perform cell count and use fresh cells or cryopreserve cells with 10% DMSO in FBS.

Surface Stain

1. Resuspend PBMC in FACS Buffer (PBS, 2% FBS, 0.1% sodium azide) at $1 \times 10^7$ cells/ml.
2. Add 200 ul of PBMC ($2 \times 10^6$ cells) to a 96 well round-bottom plate.
3. Spin cells in centrifuge for 3 minutes at 300 g.
4. Discard buffer, and add 50 ul of Fc Block Cocktail (BD; 564219); each well=2 ul Fc Block+48 ul PBS)
5. Sit plate at 4° C., covered with aluminum foil and incubate for 15 minutes.
6. Add 150 ul FACS Buffer to each well.
7. Spin cells. Spin cells in centrifuge 250 g, 3 minutes.
8. Flick supernatant into sink.
9. Gently vortex.
10. Add Alexa-MuSK or Alexa-OVA and fluorescent labeled antibody to B cell markers in 50 ul of PBS (mix cells by gently vortexing).
11. Sit plate in 4C refrigerator, covered with aluminum foil.
12. Wait 25 minutes.
13. Add 150 ul FACS buffer to each well.
14. Spin cells in centrifuge 250 g, 3 minutes.
15. Flick supernatant into sink.
16. Gently vortex.
17. Add 200 ul FACS buffer to each well.
18. Spin cells in centrifuge 250 g, 3 minutes.
19. Flick supernatant into sink.
20. Gently vortex.
21. Add 200 ul FACS buffer to each well.
22. Spin cells in centrifuge 250 g, 3 minutes.
23. Flick supernatant into sink.
24. Gently vortex.
25. Re-suspend in 200 ul of 1% PFA.
26. Cover plate in aluminum foil until acquisition by Flow Cytometry.

EXAMPLE 4

Studies in Mice

Muscle Specific Tyrosine Kinase ECD Immunization and Clinical Evaluation of Experimental Autoimmune Myasthenia Gravis Seven to eight week old wild-type C57BL6 mice (n=5) were anesthetized and immunized with 30 μg of muscle specific tyrosine kinase ECD emulsified in complete Freund's adjuvant (CFA, Difco, Detroit, Mich.) s.c. at four sites (two hind footpads and shoulders) on day 0 and were boosted with the same amount of muscle specific tyrosine kinase used in the first immunization in CFA s.c. at four sites on the back on days 28 and 56. Control mice (n=5) were immunized with only CFA. All mice were terminated 28 days after the 3rd immunization. Mice were weighed weekly and for clinical examination, mice were left for 3 minutes on a flat platform and were observed for signs of experimental autoimmune myasthenia gravis. Clinical muscle weakness was graded as follows: Grade 0, mouse with normal posture, muscle strength, and mobility; Grade 1, normal at rest, with muscle weakness characteristically shown by a hunched posture, restricted mobility, and difficulty raising the head after exercise that consisted of 30 paw grips on a cage top grid; Grade 2, grade 1 symptoms without exercise during the observation period on a flat platform; Grade 3, dehydrated and moribund with grade 2 weakness; and Grade 4, dead.

For objective measurement of muscle strength, mouse was first exercised with 40 paw grips on a cage top grid. Following exercise, mice were placed in the center of the cage top grid, stop clock was started and the grid was rotated to an inverted position over 2 sec, with the mouse's head declining first. The grid was elevated steadily 40-50 cm above a padded surface. Mouse was removed when the criterion time of 300 sec was reached and the time until it lost its grip on the grid was recorded. Clinical grading and inverted screen were done once a week.

EXAMPLE 5

Flow Cytometry to Detect Alexa-Muscle Specific Tyrosine Kinase Binding to Peripheral Blood Mononuclear Cells of Mice with Experimental Autoimmune Myasthenia Gravis At termination, PBMC were separated from the tail vein blood of mice using Lymphoprep (Axis-Shield, Oslo, Norway). Each sample was stained with antibodies labeled by immunofluorescence. In every experimental procedure, 5% fetal bovine serum in phosphate buffered saline was used to minimize non-specific binding of antibodies. Triple staining was used to label lymphocyte subgroups. Alexa 647 conjugated to muscle specific tyrosine kinase ECD (Ni-NTA agarose purified) was used at a concentration of 0.63 mg/ml to test Alexa-muscle specific tyrosine kinase (Alexa-MuSK) binding to peripheral blood mononuclear cells of mice with experimental autoimmune myasthenia gravis. Alexa-muscle specific tyrosine kinase ECD (1:200) and PE-conjugated rat monoclonal antibody to CD45R (1:100, pan-B cell marker) (Abcam, Cambridge, UK) were used to specifically label muscle specific tyrosine kinase binding B cells via the B cell receptor (surface Ig). Additionally, blood samples from each mouse were stained with FITC conjugated goat anti-mouse IgG, IgG1, IgG2b or IgG3 (1:100) (Abcam, Cambridge, UK), antibodies to detect the ratios of muscle specific tyrosine kinase binding or reactive B cells producing individual IgG isotypes. Alexa conjugated OVA was used as an antigen non-specific negative control. Appropriate isotypes were also used for anti-CD45R, IgG, IgG1, IgG2b and IgG3. Calculations were performed and analyzed by using BD FACScan (BD Biosciences, San Jose, Calif.).

Muscle specific tyrosine kinase-immunized mice had significantly lower inverted screen and weight values and higher clinical grades than CFA-immunized mice confirming that muscle specific tyrosine kinase-immunization successfully induced myasthenic muscle weakness. Muscle specific tyrosine kinase-immunized mice had significantly higher percentages of IgG2b+ B cells than CFA-immunized mice, whereas IgG, IgG1 and IgG3+ B cells were comparable between CFA- and muscle specific tyrosine kinase-immunized mice. Percentages of muscle specific tyrosine kinase-binding CD45R+, IgG+, IgG1+, IgG2b+ and IgG3+ peripheral B cells were significantly higher than those of CFA-immunized mice (Table 3).

TABLE 3

Clinical parameters and flow cytometry for
IgG isotypes, Alexa-MuSK binding PBMC (%)
in MuSK- and CFA-immunized mouse groups.

| Group | CFA | MuSK | p-value |
|---|---|---|---|
| Final inverted screen measure (sec)* | 300 ± 0 | 217.8 ± 82.9 | 0.045 |
| Final weight (gr)* | 19.9 ± 0.7 | 18.7 ± 0.6 | 0.011 |

TABLE 3-continued

Clinical parameters and flow cytometry for
IgG isotypes, Alexa-MuSK binding PBMC (%)
in MuSK- and CFA-immunized mouse groups.

| Group | CFA | MuSK | p-value |
|---|---|---|---|
| Final grade* | 0 ± 0 | 1.2 ± 1.3 | 0.054 |
| CD45R+/IgG+* | 19.3 ± 5.3 | 21.0 ± 4.9 | 0.293 |
| CD45R+/IgG1+* | 19.15 ± 6.2 | 21.58 ± 2.0 | 0.220 |
| CD45R+/IgG2b+* | 2.6 ± 2.0 | 13.0 ± 12.6 | 0.050 |
| CD45R+/IgG3* | 0.26 ± 0.23 | 0.39 ± 0.18 | 0.166 |
| CD45R+/Alexa MuSK+* | 0.2 ± 0.1 | 23.3 ± 7.2 | 0.030 |
| Alexa MuSK+/IgG+* | 0.56 ± 0.2 | 17.3 ± 16.1 | 0.026 |
| Alexa MuSK+/IgG1+* | 0.35 ± 0.2 | 14.5 ± 13.2 | 0.023 |
| Alexa MuSK+/IgG2b+* | 0.39 ± 0.3 | 14.0 ± 13.8 | 0.030 |
| Alexa MuSK+/IgG3* | 0.08 ± 0.09 | 0.31 ± 0.24 | 0.033 |

Notably, weight values showed significant inverse correlation with the ratios of muscle specific tyrosine kinase-binding CD45R+, IgG+ and IgG2b+ B cells, indicating that mice with higher muscle specific tyrosine kinase binding B cell ratios had more pronounced weight loss and thus muscle specific tyrosine kinase-reactive peripheral B cells can be used as a marker of disease severity and possibly muscle atrophy (Table 4).

TABLE 4

Correlations between clinical parameters and MuSK
binding peripheral B cell subpopulation ratios

| | | R* | P value |
|---|---|---|---|
| Weight (gr) | CD45R+/Alexa MuSK+ | −0.669 | 0.017 |
| Weight (gr) | Alexa MuSK+/IgG+ | −0.674 | 0.016 |
| Weight (gr) | Alexa MuSK+/IgG2b+ | −0.750 | 0.006 |
| CD45R+/Alexa MuSK+ | Alexa MuSK+/IgG+ | 0.659 | 2.3E−12 |
| CD45R+/Alexa MuSK+ | Alexa MuSK+/IgG2b+ | 0.838 | 3.08E−05 |
| Alexa MuSK+/IgG+ | Alexa MuSK+/IgG2b+ | 0.833 | 1.59E−05 |

*+/−SD
*correlation coefficient

Muscle specific tyrosine kinase-immunized mice showed distinct and prominent CD45R+, IgG+, IgG1+, IgG2b+ and IgG3+ B cell populations binding with Alexa-muscle specific tyrosine kinase (Alexa-MuSK) (FIGS. 3A-3I), whereas CFA-immunized mice peripheral blood mononuclear cells subgroups did not show any appreciable binding with Alexa-muscle specific tyrosine kinase (Alexa-MuSK) (FIGS. 4A-4I). Alexa-OVA did not show any remarkable binding with peripheral blood mononuclear cells subgroups of neither muscle specific tyrosine kinase nor CFA-immunized mice, suggesting that muscle specific tyrosine kinase binding to specific B cell population is antigen specific (FIGS. 5-6).

Statistics

Clinical grades were compared by Mann-Whitney U, whereas inverted screen, weight and peripheral blood mononuclear cells subpopulation percentages were compared with Student's t-test among muscle specific tyrosine kinase and CFA immunized mouse groups. Correlation statistics were performed with Pearson or Spearman methods, as appropriate.

EXAMPLE 6

Detection of MuSK-Specific B Cells in Human MuSK MG

Figure 7A:
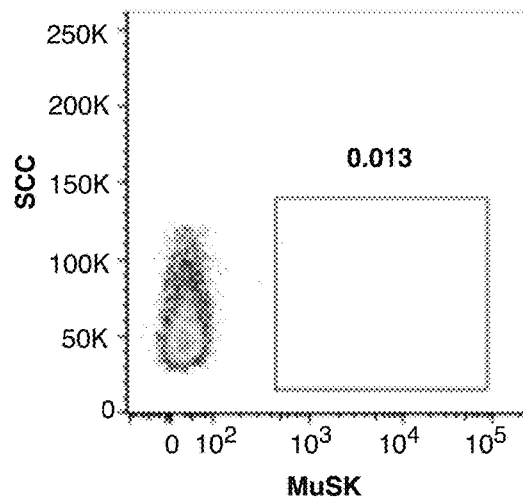
FIGS. 7A-7C show the results of detection of MuSK-specific B cells using customized muscle specific tyrosine kinase protein conjugated to Alexa 647. PBMC, from a MuSK-MG patient, was stained with and without muscle specific tyrosine kinase-Alexa 647 and analyzed by flow cytometry. Plots show B cells gated on CD19+ cells.
Figure 7B:
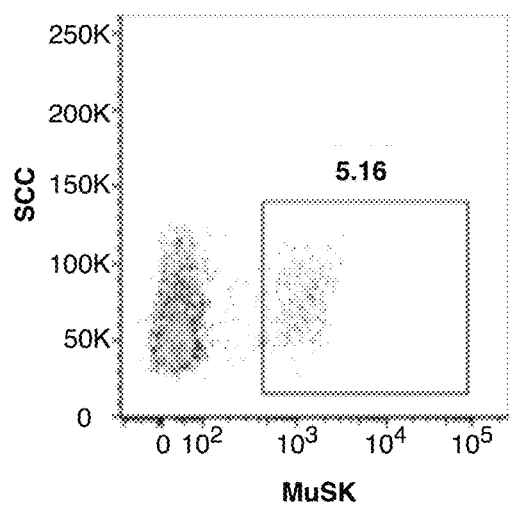
Figure 7C:
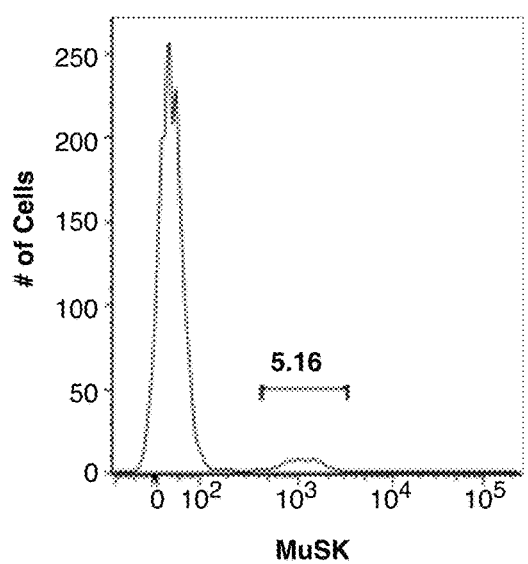

Peripheral blood was obtained by venipuncture and collected in acid-citrate-dextrose tubes. Mononuclear cells were separated by Ficoll density gradient centrifugation, washed and counted prior to storage. Cells were resuspended in a 90% FBS and 10% DMSO solution, and progressively cooled to −80° C. in a CoolCell cell freezing container. The next day the cells were transferred to liquid nitrogen for long-term storage. For flow cytometry analysis, PBMC vials were thawed in a 37° C. water bath and washed with RPMI+10% FCS. PBMCs were incubated with Fc Block for 15 minutes at 4° C. followed by surface staining with anti-CD19 PerCP Cy5.5 and muscle specific tyrosine kinase protein conjugated to Alexa647. Following a 25 minute incubation at 4° C., cells were washed three times with FACS wash (PBS + 0.5% FBS) and re-suspended with 1% paraformaldehyde prior to acquisition on a BD LSRII flow cytometer. The results are shown in FIGS. 7A-7C. Compared to the unstained control sample (FIG. 7A), the stained sample shows a differentiated cell group, which is the muscle specific tyrosine kinase-specific B cells. FIG. 7C further confirms that there is a group of muscle specific tyrosine kinase-specific B cells identified, which is much larger than the majority of cells.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined.

What is claimed is:

1. A method for diagnosing muscle specific tyrosine kinase autoimmune myasthenia gravis in an individual, comprising the steps of:
   obtaining a sample comprising B cells from said individual and from a healthy control individual;
   contacting said individual sample and said healthy control sample with a conjugate comprising an extracellular domain of a muscle specific tyrosine kinase comprising SEQ ID NO: 1 coupled to a fluorophore; and
   measuring a level of muscle specific tyrosine kinase binding to B cells in said individual sample, wherein at least a 2 fold increase in the level of muscle specific tyrosine kinase reactive B-cells compared to the level of muscle specific tyrosine specific kinase reactive B-cells in the healthy control sample indicates the presence of muscle specific tyrosine kinase autoimmune myasthenia gravis.

2. The method of claim 1, wherein said individual sample and said healthy control sample are blood samples or purified peripheral blood cells.

3. The method of claim 1, wherein the measuring step is by flow cytometry.

4. The method of claim 1, further comprising the steps of:
   administering a therapy to a patient with myasthenia gravis or experimental autoimmune myasthenia gravis;
   measuring an amount of muscle specific tyrosine-reactive B cells in peripheral blood mononuclear cell samples from the muscle specific tyrosine kinase myasthenia gravis patient after said therapy, wherein a depletion of muscle specific tyrosine kinase-reactive B cells indicates a positive response of said patient to the therapy.

5. A method for diagnosing muscle specific tyrosine kinase autoimmune myasthenia gravis in an individual, comprising the steps of:
   obtaining a sample comprising B cells from said individual and from a healthy control individual;
   contacting the individual sample and the healthy control sample with a conjugate comprising an extracellular domain of muscle specific tyrosine kinase comprising SEQ ID NO: 1 coupled to a fluorophore;
   contacting the individual sample and the healthy control sample with an antibody that binds B cells and
   measuring the levels of said muscle specific tyrosine kinase and said antibody that bind to the B cells from said individual sample and from said healthy control sample, wherein an increase in the binding levels in the individual sample compared to the binding levels in the healthy control indicates increased muscle specific tyrosine kinase specific B cells that produces pathogenic muscle specific tyrosine kinase antibodies for muscle specific tyrosine kinase myasthenia gravis.

6. The method of claim 5, wherein the antibody binds IgG, IgG1, IgG2, IgG3, IgG4, CD19, CD21, CD45R, CD20, CD22, CD23, or CD81.

7. The method of claim 1 wherein the fluorophore is an Alexa fluorophore.

8. The method of claim 7 wherein the Alexa fluorophore is Alexa-488 or Alexa-647.

9. The method of claim 5 wherein the fluorophore is an Alexa fluorophore.

10. The method of claim 9 wherein the Alexa fluorophore is Alexa-488 or Alexa-647.

* * * * *

SEQUENCE LISTING

```
<160> NUMBER OF SEQ ID NOS: 1

<210> SEQ ID NO 1
<211> LENGTH: 488
<212> TYPE: PRT
<213> ORGANISM: Artificial sequence
<220> FEATURE:
<221> NAME/KEY: PEPTIDE
<223> OTHER INFORMATION: Extracellular domain of human muscle specific
      tyrosine kinase

<400> SEQUENCE: 1

Glu Phe Leu Pro Lys Ala Pro Val Ile Thr Thr Pro Leu Glu Thr Val
1               5                   10                  15

Asp Ala Leu Val Glu Glu Val Ala Thr Phe Met Cys Ala Val Glu Ser
                20                  25                  30

Tyr Pro Gln Pro Glu Ile Ser Trp Thr Arg Asn Lys Ile Leu Ile Lys
            35                  40                  45

Leu Phe Asp Thr Arg Tyr Ser Ile Arg Glu Asn Gly Gln Leu Leu Thr
        50                  55                  60

Ile Leu Ser Val Glu Asp Ser Asp Asp Gly Ile Tyr Cys Cys Thr Ala
65                  70                  75                  80

Asn Asn Gly Val Gly Gly Ala Val Glu Ser Cys Gly Ala Leu Gln Val
                85                  90                  95

Lys Met Lys Pro Lys Ile Thr Arg Pro Pro Ile Asn Val Lys Ile Ile
                100                 105                 110

Glu Gly Leu Lys Ala Val Leu Pro Cys Thr Thr Met Gly Asn Pro Lys
            115                 120                 125

Pro Ser Val Ser Trp Ile Lys Gly Asp Ser Pro Leu Arg Glu Asn Ser
        130                 135                 140

Arg Ile Ala Val Leu Glu Ser Gly Ser Leu Arg Ile His Asn Val Gln
145                 150                 155                 160

Lys Glu Asp Ala Gly Gln Tyr Arg Cys Val Ala Lys Asn Ser Leu Gly
                165                 170                 175

Thr Ala Tyr Ser Lys Val Val Lys Leu Glu Val Glu Val Phe Ala Arg
                180                 185                 190

Ile Leu Arg Ala Pro Glu Ser His Asn Val Thr Phe Gly Ser Phe Val
            195                 200                 205

Thr Leu His Cys Thr Ala Thr Gly Ile Pro Val Pro Thr Ile Thr Trp
        210                 215                 220
```

-continued

```
Ile Glu Asn Gly Asn Ala Val Ser Ser Gly Ser Ile Gln Glu Ser Val
225                 230                 235                 240

Lys Asp Arg Val Ile Asp Ser Arg Leu Gln Leu Phe Ile Thr Lys Pro
                245                 250                 255

Gly Leu Tyr Thr Cys Ile Ala Thr Asn Lys His Gly Glu Lys Phe Ser
            260                 265                 270

Thr Ala Lys Ala Ala Ala Thr Ile Ser Ile Ala Glu Trp Ser Lys Pro
        275                 280                 285

Gln Lys Asp Asn Lys Gly Tyr Cys Ala Gln Tyr Arg Gly Glu Val Cys
    290                 295                 300

Asn Ala Val Leu Ala Lys Asp Ala Leu Val Phe Leu Asn Thr Ser Tyr
305                 310                 315                 320

Ala Asp Pro Glu Glu Ala Gln Glu Leu Leu Val His Thr Ala Trp Asn
                325                 330                 335

Glu Leu Lys Val Val Ser Pro Val Cys Arg Pro Ala Ala Glu Ala Leu
                340                 345                 350

Leu Cys Asn His Ile Phe Gln Glu Cys Ser Pro Gly Val Val Pro Thr
            355                 360                 365

Pro Ile Pro Ile Cys Arg Glu Tyr Cys Leu Ala Val Lys Glu Leu Phe
370                 375                 380

Cys Ala Lys Glu Trp Leu Val Met Glu Glu Lys Thr His Arg Gly Leu
385                 390                 395                 400

Tyr Arg Ser Glu Met His Leu Leu Ser Val Pro Glu Cys Ser Lys Leu
                405                 410                 415

Pro Ser Met His Trp Asp Pro Thr Ala Cys Ala Arg Leu Pro His Leu
            420                 425                 430

Ala Phe Pro Pro Met Thr Ser Ser Lys Pro Ser Val Asp Ile Pro Asn
        435                 440                 445

Leu Pro Ser Ser Ser Ser Ser Ser Phe Ser Val Ser Pro Ala Ala Ala
    450                 455                 460

Ser Phe Leu Glu Gln Lys Leu Ile Ser Glu Glu Asp Leu Asn Ser Ala
465                 470                 475                 480

Val Asp His His His His His His
                485
```